United States Patent [19]
Plummer

[11] Patent Number: 5,097,132
[45] Date of Patent: Mar. 17, 1992

[54] NUCLEAR MEDICINE CAMERA SYSTEM WITH IMPROVED GANTRY AND PATIENT TABLE

[75] Inventor: Steven J. Plummer, Hudson, Ohio

[73] Assignee: Picker International, Inc., Highland Hts., Ohio

[21] Appl. No.: 616,985

[22] Filed: Nov. 21, 1990

[51] Int. Cl.$^5$ .............................................. H05G 1/02
[52] U.S. Cl. .................. 250/363.08; 378/20
[58] Field of Search ...................... 250/363.08, 363.05, 250/363.02; 378/20, 208, 209

[56] References Cited

U.S. PATENT DOCUMENTS 4,928,283  5/1990  Gordon ................................ 378/20

OTHER PUBLICATIONS

Triad Spect System; Trionix Research Laboratories, Inc. 1988.
Capintec, Inc., CAPTURA System Advertising Brochure 1989.
ECAT Advertisement; Siemens Medical Systems, Inc.
PRISM Advertisement; Ohio Imaging, Inc. 1988.
Technology Update; Shimadzu Medical System's Headtone SE T-031, Jun. 1989.

*Primary Examiner*—Janice A. Howell
*Assistant Examiner*—Richard Hanig

*Attorney, Agent, or Firm*—Fay, Sharpe, Beall, Fagan, Minnich & McKee

[57] ABSTRACT

A patient table assembly (10) is fixedly mounted on pedestals (14, 16) with a table top (12) passing through a central aperture (116) of a rotatable inner gantry (110). The inner gantry (110) is rotatably mounted in an outer gantry (80) which selectively moves parallel to the table top along tracks (82). The foot end pedestal (14) has an arm (30) and a flange and contour block arrangement (36) which receives a foot end (40) of the table top fixedly therebetween. A slide (58) clamps the head end of the table top to an arm (50) connected with the second pedestal. A front wheel carriage (90) includes a pair of wheels (98) which are rotatably mounted to a pivot member (92) for limited rotation about the outer gantry (80). Detector heads (112, 114) are mounted to slide members (132, 136,156,158) which slide on guide members (134, 138). A motor (140, 152) and acme screw (142, 154) drive one slide along the guide members. Flexible cables (174, 190) prevent a free side slide from canting the detector head under the force of gravity. Electrical or fluid cables (202, 204) from the detector heads pass around rollers (210, 212). A wire rope (218) has its opposite ends connected with the rollers and a generally central portion connected by a block and tackle (222) with a gas spring (216).

34 Claims, 9 Drawing Sheets

NUCLEAR MEDICINE CAMERA SYSTEM WITH IMPROVED GANTRY AND PATIENT TABLE

BACKGROUND OF THE INVENTION

The present invention relates to medical imaging systems. It finds particular application in conjunction with nuclear or gamma camera systems in which the gantry moves relative to a fixed patient table and will be described with particular reference thereto. However, it is to be appreciated, that the invention will also find application in conjunction with nuclear camera and diagnostic scanners of other types and designs such as PET scanners, digital x-ray equipment, CT scanners, and the like.

Heretofore, nuclear gamma cameras have included a detector head which receives radiation emanating from the patient. The head includes a flat scintillation crystal which converts incident radiation to flashes of light. Internal electronics convert each flash of light into an indication of the location and energy of each received incident radiation event. Typically, the detector head is housed in a radiation blocking material, such as a lead housing, and weighs several hundred pounds.

Various table and gantry systems have been provided which enable one or more detector heads to be positioned at selected locations relative to the patient. For some medical procedures, the head is stationarily positioned over the patient's chest or other examined body area. In other medical procedures, one detector head moves just above and along a longitudinal axis of the patient. When a second head is provided, it generally moves concurrently below the patient and along the longitudinal axis. In this manner, whole body scan information is provided. When a medical procedure is performed which calls for a tomographic type scan, one or more camera heads are rotated around the longitudinal axis. Typically, the detector heads move toward and away from the patient as they rotate, rather than rotating along a circular path, to minimize distance between the detector head and the patient.

Various gantry and table top systems have been provided for facilitating the relative movement of the detector head and the patient, for assuring that the detector heads are at the appropriate, non-canted position relative to the patient, for maintaining tension on cables during detector head movement, and the like.

In one of the prior art gantry systems, each head is mounted on a pair of arms. The arms are centrally pivotally on a large diameter bearing ring with a counterweight at the other end. Although the counterweights reduce the effective weight of the camera head, the length of the cantilevered arms require the gantry to consume a relatively large area. Moreover, moving counterweights tends to be a safety hazard to operator personnel.

Another prior art camera mounts the head pivotally to a single arm with appropriate control mechanisms to move and rotate the arm and head. By eliminating the counterweights, space is saved. However, the large weight of the heads necessitates solid parts and strong drive mechanisms.

The patient support table is typically supported adjacent one end in a cantilever fashion in order to accommodate both longitudinal and circumferential movement of multiple detector heads without the support interfering with head movement. One of the problems with a table top that is cantilevered from one end is that it tends to deflect and oscillate. The maximum deflection for a cantilevered table is described mathematically as $WL^3/8EI$, where E is elasticity, I is the moment of inertia, L is the length, and W is the load.

In another prior art system, the head is mounted for longitudinal movement along an elongated horizontal beam. The beam is connected at opposite ends for rotation around the circumference of the patient.

In another prior art system, the patient is received along an axis of a pair of spaced, parallel large diameter bearings. A camera head and a counterweight are connected with the bearings 180° apart. Alternately, a second head is connected with the inner race diametrically opposite the first head.

In such systems, the patient table is either cantilevered or simply supported at opposite ends. When the patient table is simply supported, i.e. supported to permit relative pivotal movement between the table and end supports, the gantry and detector heads are typically moved both longitudinally and rotationally with respect to the patient. The simply supported table deflects much less than the cantilevered table. The maximum deflection for the simply supported table is described mathematically by $5WL^3/384EI$.

The maximum stress for a cantilevered table top is about four times the maximum stress for a simply supported system. In order to minimize deflection and to provide sufficient strength to withstand the stress, simply supported table systems are relatively thick and cantilevered tables are even thicker. The thickness of the table top increased radiation absorption, increases the minimum patient to detector head distance, increases cost, and reduces the amount of radiation received by a detector head disposed below the patient.

The detector heads, being several hundred pounds, tend to become canted during movement. The effects of gravity and the large mass cause supporting posts to shift or deflect, particularly if the head is not supported and driven on both sides. This causes an increase in support structure, more complexity, and a duplication of drives.

Some of the prior art gantry systems are mounted on rails to move relative to a stationary patient. Typically, these gantry systems are supported on three or four wheels. Four or more wheels require precise adjustment of the wheels and precisely flat rail surfaces, lest the gantry rock. One of the problems with a three wheel support system is that the gantry was supported on one side by only a single wheel. The single wheel leads to potential instability and tipping problems.

Cables interconnect each detector head with stationary electronic circuitry. In a dual head camera, a separate take up mechanism is typically provided for handling the cable extending from the heads during rotation. The cable handling system uses a variety of guides, springs, or counterweights for fixing the position and tension of the cables continuously during motion to prevent tangling, kinking, or undue stress on the cables. Depending on the diameter over which the detector heads are rotated, the cable take up mechanism may have several feet more slack at some orientations of the head than others. In one cable take up assembly, each cable passed over a pair of pulleys and had a weight mounted by a pulley therebetween. As the cable lengthened and contracted, the weight carrying pulley moved up and down, analogous to an elevator. This arrangement kept a constant tension on the cables, but required a large area within which the weight mounted pulley could move. A similar assembly was required for the cable from the other head. In other take up mechanisms, the weight was replaced by a spring. The spring enabled the pulley to travel along horizontal or other non-vertical paths, but still required an intended region for accommodating the cable as it was played in and pulled out.

The present invention contemplates a new and improved gantry and table system which overcomes the above-referenced problems and others.

SUMMARY OF THE INVENTION

In accordance with one aspect of the present invention, a patient table is fixedly mounted to supports at both ends which are stationarily mounted to the floor. An outer gantry is disposed between the supports for movement longitudinally along the patient table. An inner gantry is rotatably mounted on the outer gantry for selectively moving one or more detector heads circumferentially around the longitudinal axis and closer and further away from the patient.

In accordance with a more limited aspect of the present invention, the support at one end of the patient table includes a first fixed support arm upon which the one end of the table rests and a flange disposed above the support arm for holding the table one end therebetween. The support at the other end includes a second fixed support arm on which the second end of the table rests. A clamp means selectively clamps the table other end to the second support cantilevered arm.

In accordance with another aspect of the present invention, a single drive mechanism is provided for translating the detector head along a pair of parallel guide bars. The drive mechanism is connected with a driven side of the detector head. A chain or other flexible drive arrangement connects the driven and free sides of the head to assure that both sides move uniformly, without canting.

In accordance with another aspect of the present invention, the gantry is moveable along rails positioned on the floor. The gantry is supported at least at one point by a wheel carrying carriage that carries at least a pair of wheels. The carriage is rotatably mounted to the gantry to assure that both carriage wheels are firmly on the track. Pivotal movement of the carriage is limited to a selected range to prevent the gantry from tipping.

In accordance with another aspect of the present invention, a single take up spring mechanism is provided for two cables from the detector heads. The cables pass around a pulley arrangement. The two pulley arrangements are connected by a flexible connection with a single spring mechanism. More specifically to the preferred embodiment, the flexible interconnection passes over a block and tackle means for multiplying the extension of the spring. Because a continuous flexible connection interconnects both take up pulleys, each cable may extend and contract independently.

In accordance with a more limited aspect of the present invention, the spring is a gas spring.

One advantage of the present invention is that it produces better diagnostic images. The table top undergoes significantly less deflection than both simply supported and cantilevered tops reducing oscillating and misalignment between the detector head and the patient.

Another advantage of the present invention is that the detector head receives more radiation when disposed below the patient. Because the fixed support system suffers less stress that either the simply supported or cantilevered systems, i.e. is stronger, the table top is significantly thinner reducing radiation absorption.

Another advantage of the present invention is that it improves the stability of detector heads and translating gantries.

Another advantage of the present invention is that is simplifies and reduces the space required for cable take up and tensioning mechanisms.

Still further advantages of the present invention will become apparent to those of ordinary skill in the art upon reading and understanding the followed detailed description of the preferred embodiments.

BRIEF DESCRIPTION OF THE DRAWINGS

The invention may take form in various parts and arrangements of parts, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
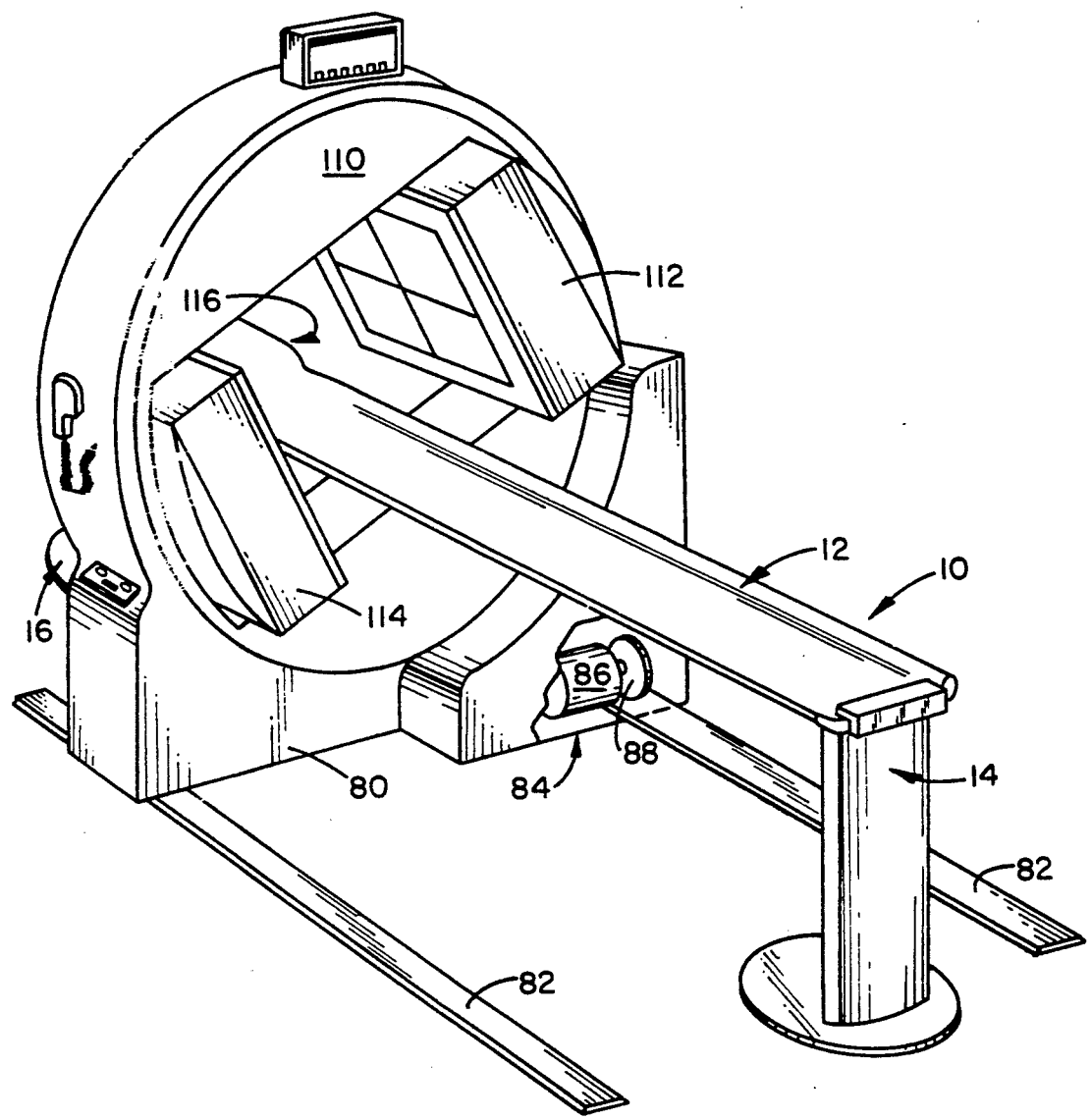
FIG. 1 is a perspective view of a gamma camera gantry and patient support table in accordance with the present invention.
Figure 2:
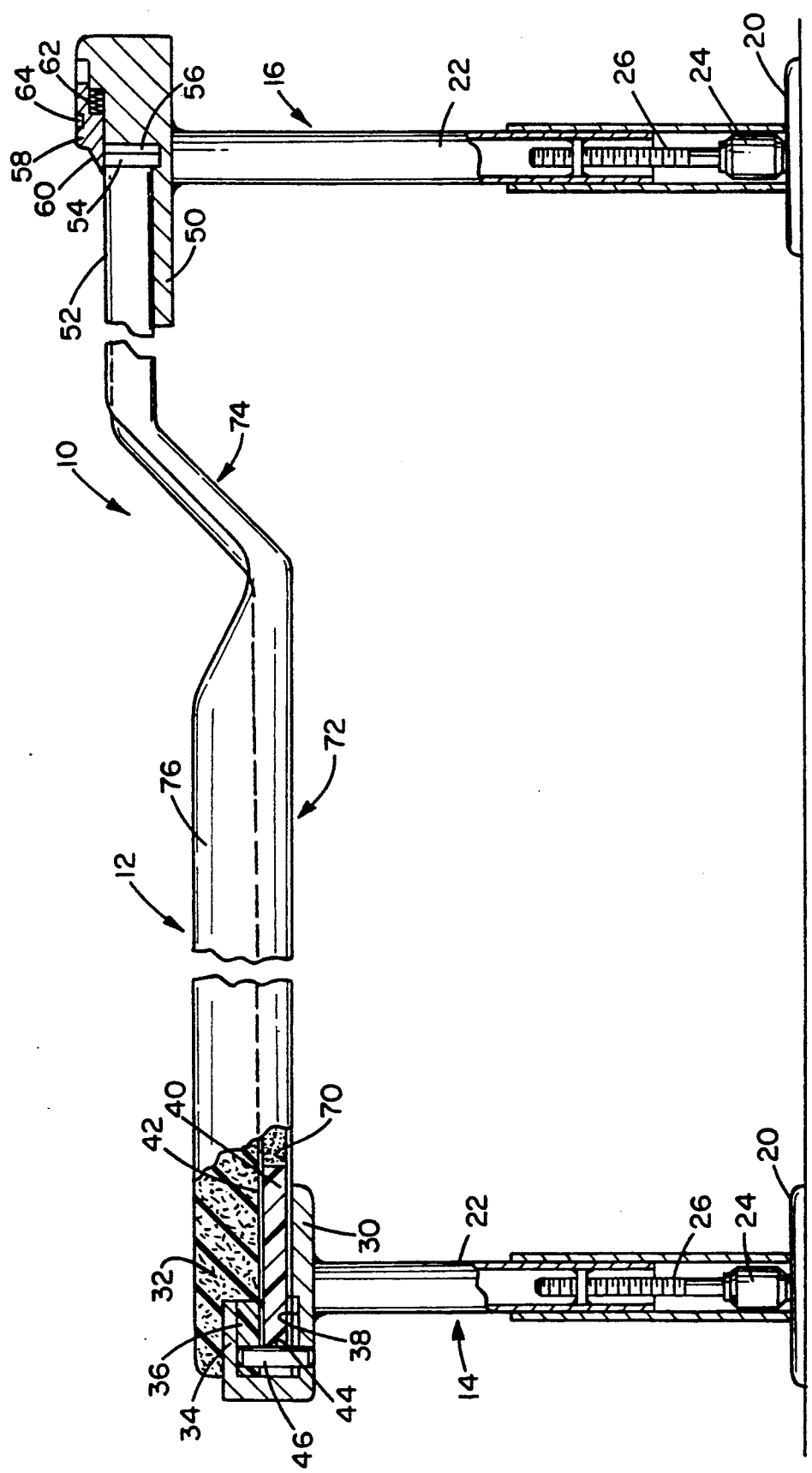
FIG. 2 is a side view in partial section of a patient support table and fixed head and foot end supports.
Figure 3:
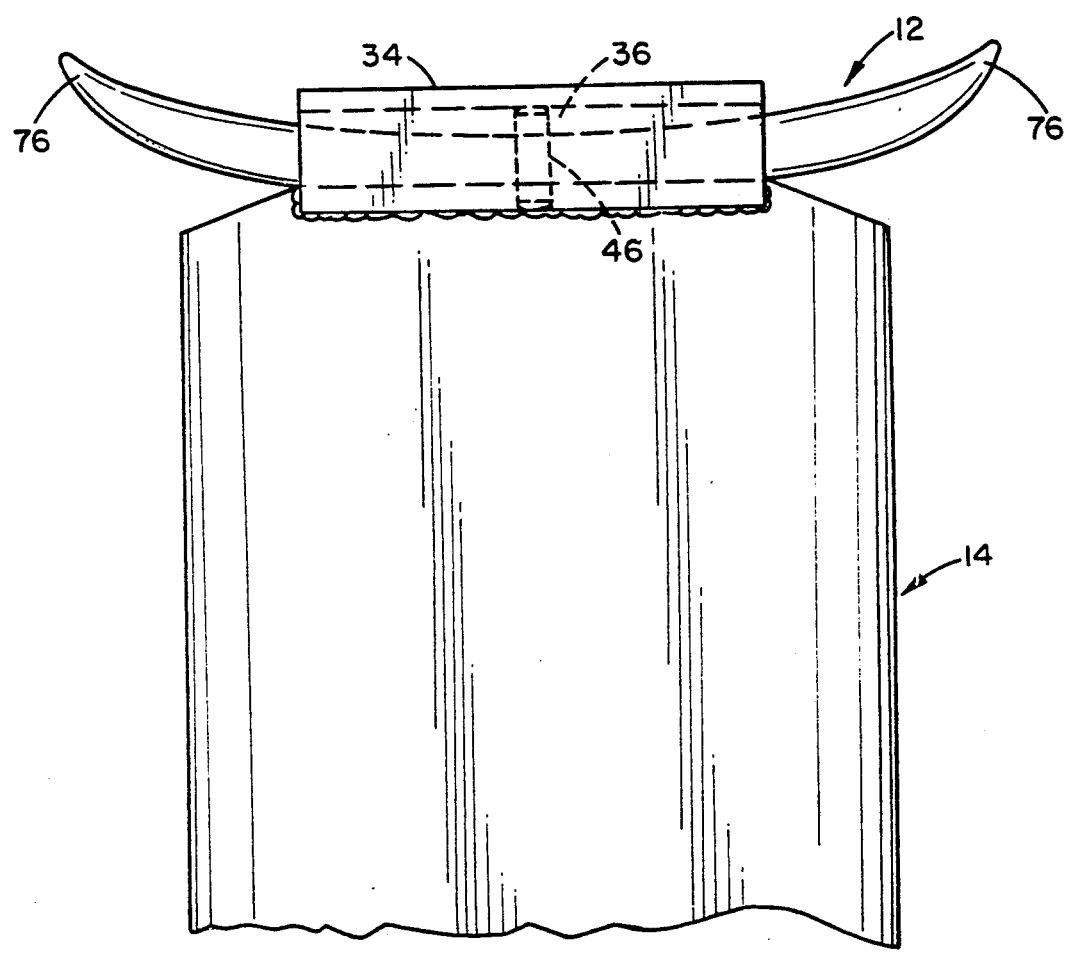
FIG. 3 is an end view from the foot end of the patient table of FIG. 2.
Figure 4:
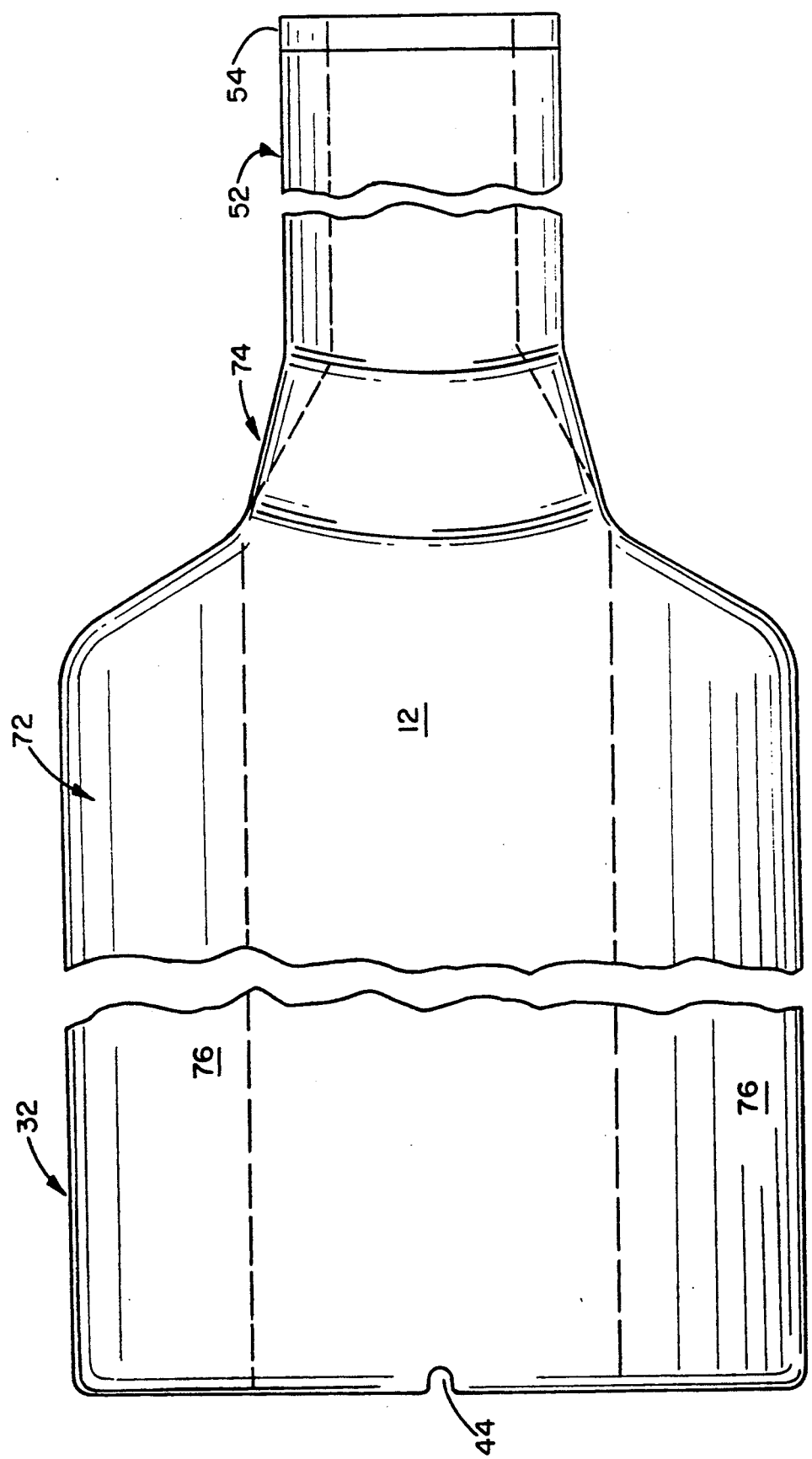
FIG. 4 is a top view of the table of FIG. 2.
Figure 5B:
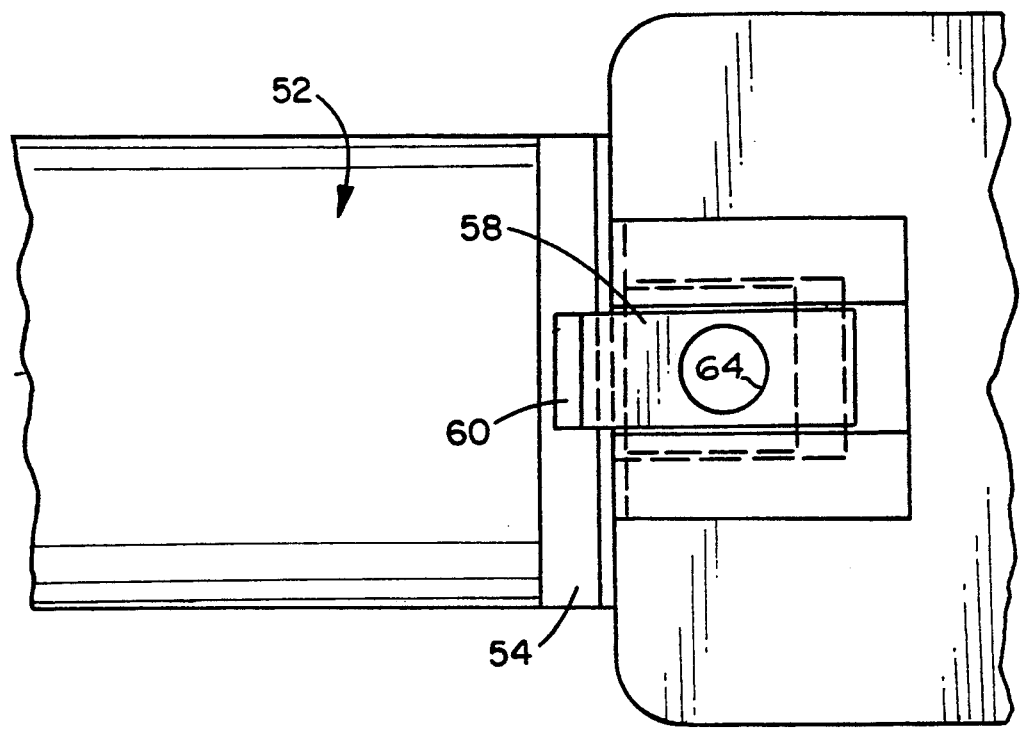
FIGS. 5A and 5B are side and top views of the head end table top latching arrangement of FIG. 2.
Figure 5A:
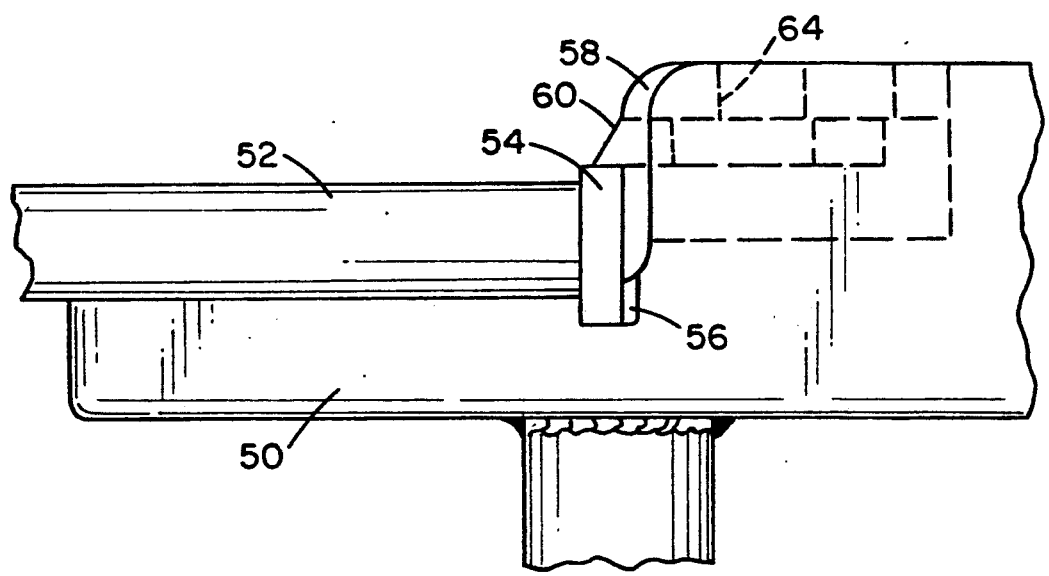

With reference to FIGS. 1-5, a patient table assembly 10 includes a top or patient support 12 and a pair of end vertical supports or pedestals 14, 16 which are fixedly mounted to the floor. The top is fixed at each end to one of the pedestals. The first and second supports each include a floor mounted portion 20 in which a top supporting portion 22 is telescopically received. A drive motor 24 and threaded screw 26 selectively raises and lowers the top supporting portion. The drive motors of both the head and foot end supports 14, 16 are electrically connected together such that both ends of the table are always raised and lowered concurrently.

The telescoping portion 22 of the foot support pedestal 14 carries a means for fixedly mounting one end of the top. In the illustrated embodiment, the fixed mounting means includes a rigidly mounted cantilevered support arm 30 that has an upper support surface on which a foot end 32 of the table top 12 is supported. An upper flange 34 is spaced from the support arm a sufficient distance to receive the foot end of the patient table snugly therebetween. A contoured block 36 conforms the effective shape of the flange 34 to the upper surface of the foot end of the table top. A well or clearance area 38 enables the table top to be tipped slightly as it is inserted under the flange and contour block 36 into a firm fit therewith.

The foot end of the table has relatively rigid and non-compressive core 40 which is surrounded by a graphite skin 42. A notch or cut out 44 is defined centrally in the table foot end for receiving a centering member or pin 46 extending downward from the flange and contour block 36. The alignment pin 46 and notch 44 assure that food end of the top is accurately positioned, fully received, and fixedly supported. The pin and notch prevent horizontal sliding or shifting of the top.

The telescopically received portion 22 of the head supporting podium ±6 carries a means for fixedly mounting the other end of the top. In the illustrated embodiment, the fixed mounting means includes a support arm 50 whose upper surface is contoured to match a lower surface of a head end 52 of the table top 12. The head end of the top includes rigid block portion 54 that is received in a groove 56 in the support arm 50. A slider 58 with a chamfered upper leading edge 60 locks the block portion in the groove. The slider is biased by a spring 62 into its top fixing position. A recess 64 facilitates manual withdrawal of the slider to remove the top.

To mount the top, the foot end 32 is inserted between the support arm 30 and the flange 34 such that the notch 44 engages the pin 46. As the head end 52 is lowered toward support arm 50, the block portion 54 engages the chamfered edge 60. The slide is cammed back against the spring bias allowing the block to continue into the groove 56. When the head end is fully lowered, the slide is spring biased forward into engagement with the top of the block. To remove the top, the operator moves the slide rearward and raises the head end.

Between the head and foot end support arms, the table top 16 has a thin foam core 70 which is covered by the carbon fiber skin 42. With the fixed end mounting described above, the maximum deflection for the table top is described mathematically as $WL^3/384EI$, i.e. five times better than a simply supported system and about 48 times better than a cantilevered system. Analogously, the maximum stress is only about three quarters of the maximum stress for a simply supported system and about one sixth of the stress for a cantilevered system.

The significant reduction in both deflection and stress renders the assembly much stronger. Less strength is needed in the table top itself. Accordingly, the table top is thinner than in the simply supported systems and significantly thinner than in the cantilevered systems with no loss in strength or resistance to deflection. In the preferred embodiment, the thickness of the table top is reduced to between one half and three quarters of the thickness of the table top of a comparable simply supported system.

The table top 12 includes a body supporting portion 72, a stepped neck region 74, and the head supporting region 52. The head and neck supporting region are relatively narrow with minimal arcing. The body supporting region 72 is significantly wider and has arced flanges 76 at either side to assure that the patient remains positioned on the table.

With reference again to FIG. 1, an outer gantry 80 is movably mounted on tracks 82 which extend parallel to the longitudinal axis. An outer gantry moving means 84 selectively moves the outer gantry so along the rails 82 in a path parallel to the longitudinal axis of the table assembly 10. In the illustrated embodiment, the longitudinal moving means includes a motor 86, selectively drives a wheel 88 which frictionally engages the track and drives the gantry therealong.

Figure 6:
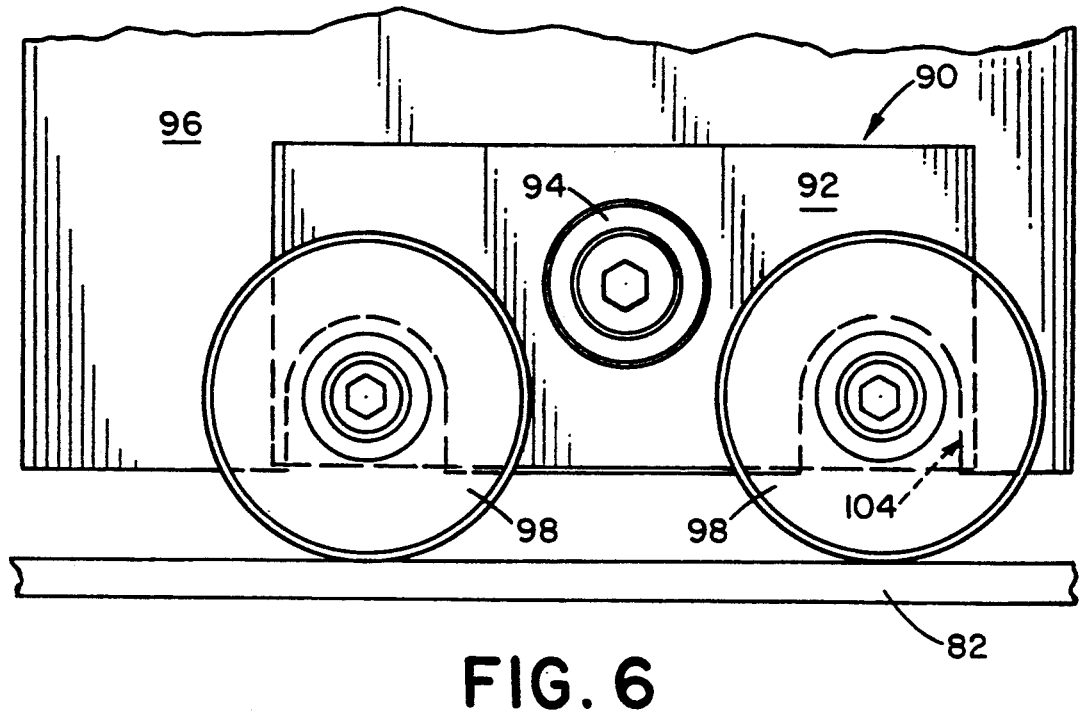
FIG. 6 is a front view of a gantry wheel assembly.
Figure 7:
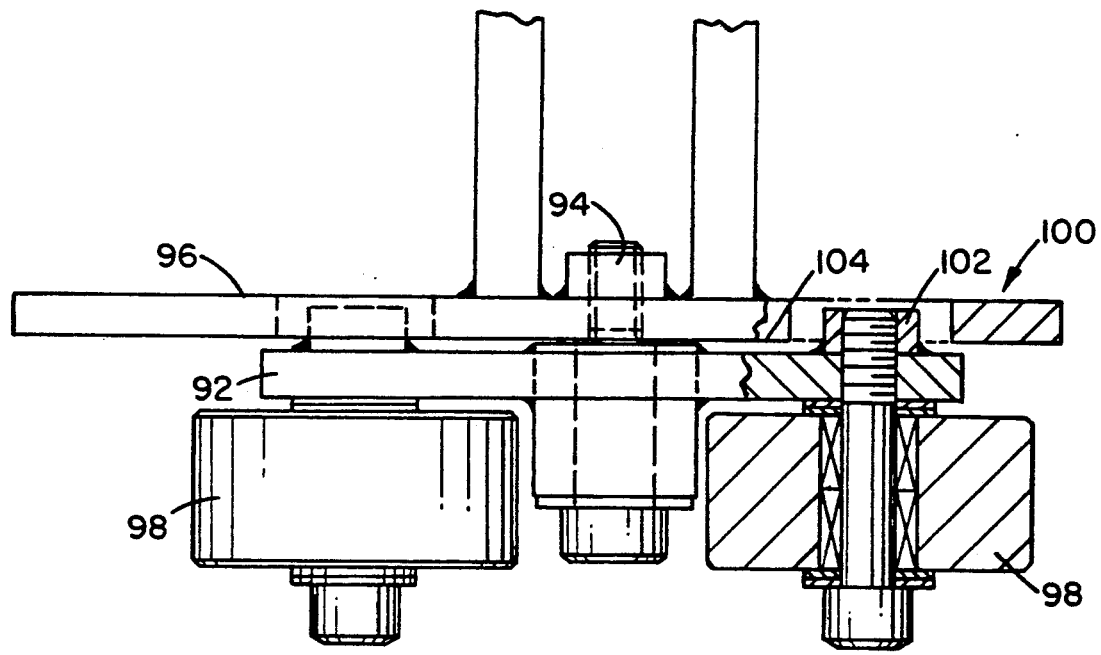
FIG. 7 is a top view and partial section of the wheel assembly of FIG. 6.

With reference to FIGS. 6 and 7, a forward wheel assembly or carriage 90 includes a pivot plate or carriage member 92 fixedly mounted by a pivot 94 to a front frame portion 96 of the outer gantry so. A pair of wheels 98 are rotatably connected with the pivot plate 92 by appropriate bearings. A rotation limiting means 100 limits pivotal movement of the plate 92. In the preferred embodiment, the pivot limiting means includes rearward extensions 102 from each of the wheels 98 and complementary receiving recesses 104 in the frame portion 96. The recesses in the frame portion are spaced a short distance from the rearward extensions such that the plate 92 and wheels can rock a small amount before the extensions 102 and frame 96 engage. Various other rotation limiting means are contemplated, such as an arcuate slot and pin arrangement.

In this manner, the pair of front wheels 98 and two rear wheels share in carrying the weight of the gantry. The limited pivotal movement of the carriage assures that all four wheels will securely rest on the floor, even if there are irregularities in the floor or track 82. Moreover, the wider the wheels 98 are spaced, the more stable the gantry becomes, i.e. the further the center of gravity must shift before the gantry tips over.

With reference again to FIG. 1, an inner or rotating gantry 110 is rotatably mounted on the outer gantry 80. A first camera or detector head 112 is movably mounted to the inner gantry. A second detector head 114 is movably mounted to the inner gantry opposite to the first camera head. The inner gantry defines a central, patient receiving aperture 116 for receiving the patient table top 12 and, a supported patient along the longitudinal axis. The aperture 116 is enlarged to receive the detector heads in any of a variety of displacements from the longitudinal axis and any of a variety of angular orientations to the axis.

Each detector head includes a scintillation crystal that emits a flash of light in response to incident radiation. An array of photomultiplier tubes convert each light flash into a corresponding electrical signal. A resolver circuit resolves (x,y) coordinates of each light flash and the energy of the incident radiation. After appropriate uniformity and linearity correction, the count or number of flashes at each (x,y) coordinate is converted to gray scale and displayed on a CRT or video monitor.

Figure 8:
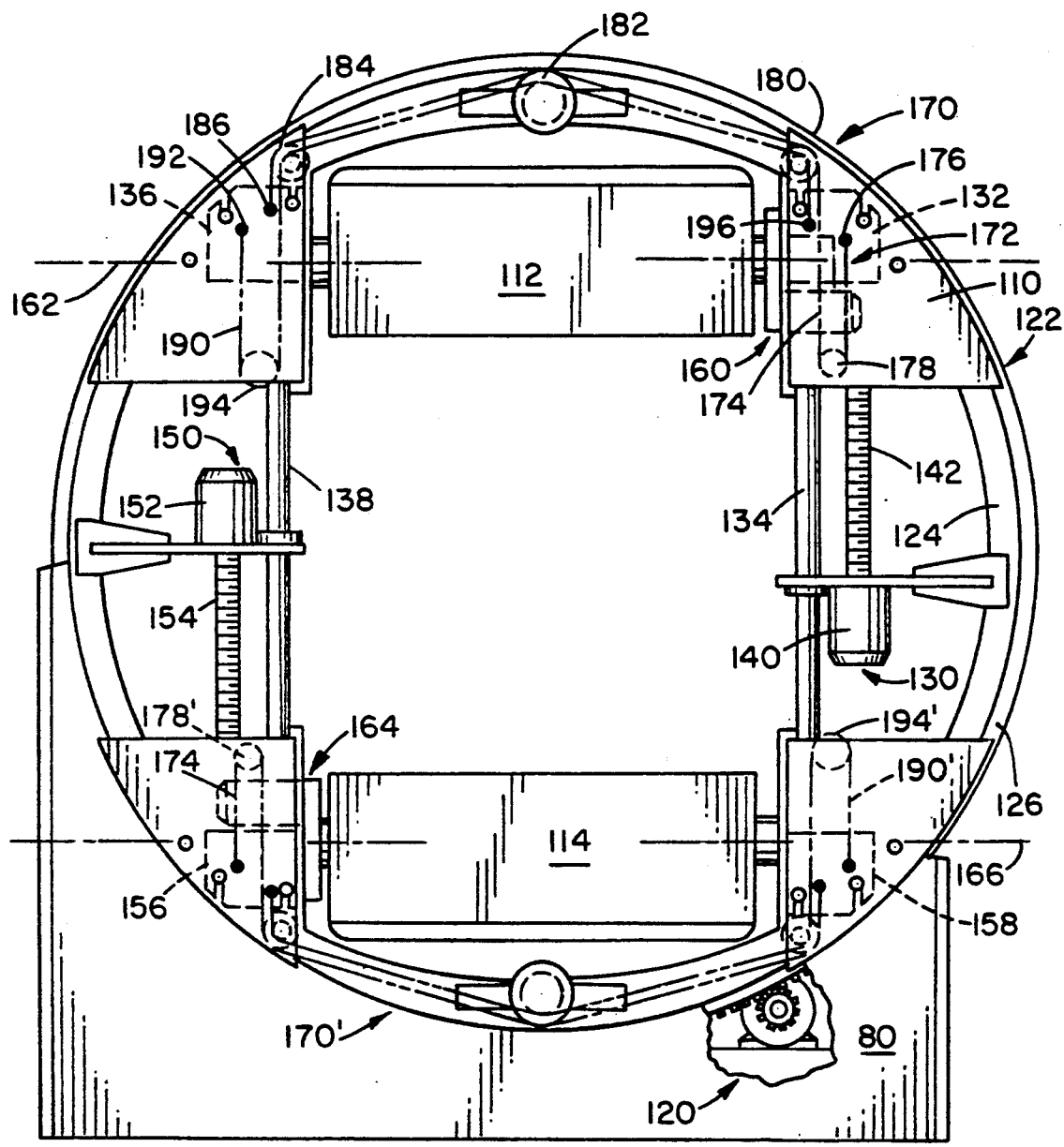
FIG. 8 illustrates internal portions of the inner gantry, particularly portions for mounting and translating the detector heads.

With reference to FIG. 8, an inner gantry rotating means 120 rotates the inner gantry 110 relative to the stationary outer gantry 80. The inner gantry rotating means 120 includes a large diameter bearing 122 having an inner race 124 and an outer race 126. The inner bearing race 124 extends peripherally around the inner gantry 110 and is a main structural member thereof.

A large diameter gear is connected with the inner race for rotation therewith. An electric motor mounted to the outer gantry, provides rotational energy to a gear that meshes with the large diameter gear. By applying motive force with motor, the inner gantry and associated detector heads are caused to rotate around the longitudinal axis.

A first head translating means 130 selectively moves or translates the first detector head 112 toward and away from the longitudinal axis. The detector head is connected with a first or drive side carriage or slide 132 that slides on a first guide rod or member 134 and second or free side carriage or slide 136, that slides on a second guide rod or member 13B. A motor 140 rotates a drive screw 142 that is threadedly received through the driven side carriages 132. By selectively providing energy to the motor 140, the carriages 132, 136 slide along guide rods 134, 138.

A second head translating means 150 selectively translates or moves the second detector head 114 along the guide members 134, 138. A motor 152 rotates a drive screw 154 that is threadedly received in a driven slide carriages 156. By selectively providing energy to the motor 152, the driven slide carriage 156 and a free side slide carriage 158 slide along the rods 134, 138 translating the second detector head.

A first detector head angular position adjusting means 160 selectively rotates the first detector head 112 about a first axis 162. The first head is mounted to the slide carriages by shafts which are rotatably received in bearings in the slide carriages. A motive power means, such as a motor mounted to one of the carriages, provides motive power through a gear or chain assembly to rotate the mounting shaft portions hence the first detector head.

A second detector head angular position adjusting means 164 rotates the second detector head 114 about a second axis 166. The second head is mounted to shaft portions which are received in bearings in carriages &:o permit the shaft portions and detector head to rotate around the second axis 166. A motive power means, such as a motor mounted on one of the carriages, provides motive power through a gear or chain assembly to rotate the shaft portions, hence the detector head. The first and second axes are disposed in a plane which is transverse to the longitudinal axis.

With this arrangement, the inner gantry rotating means 120 rotates the detector heads continuously or incrementally around the patient. The heads can be positioned stationarily at any angular increment around the longitudinal axis. The first and second detector head angular position means 160, 164 independently adjust the angular position of the first head 112 about the first axis 162 and the second head 114 about the second axis 166. The first head translating means 130 and the second head translating means 150 selectively move the first and second heads, independently, closer to and further from the patient table 10.

Although the carriages or slides 132, 136, 156, 158 fix the position of the detector heads relatively securely on the guides, the detector heads are heavy, typically several hundred pounds. As the detector head rotates, the free end of the detector head tends to shift. Where the inner carriage is rotated 180° with the guide members 134, 138 extending horizontally, detector heads 112, 114, are disposed along an axis perpendicular to the guide members. As the inner gantry is rotated, the free side slide carriages tend to slide along the associated guide members in a downward direction. The component of downward force increases with inner carriage rotation until the guide members are disposed vertically.

To prevent the free side of the first detector head 112 from sagging, a first detector head canting eliminating means 170 is provided. A like second detector head canting eliminating means 170' prevents the free side of the second detector head 114 from sagging. Because the second detector head canting eliminating means is the same as the first detector head canting eliminating means, it will be described by the same reference numerals but followed by a prime (') and it will be understood that the description applies to both.

The canting eliminating means 170 includes a first cable assembly 172 for preventing the free end from sagging toward the center. A first flexible member such as a leaf chain 174 has a first end 176 connected with the driven end slide carriage 132. The chain extends parallel to the guide member 134 to a first pulley 178 that is fixedly mounted to the inner gantry 110. The chain extends over sprocket or pulley means 180, 182, and 184 around the peripheral end of the guide members and detector head. From sprocket or pulley means 184, the first chain or flexible member extends parallel to the guide member 138 to a second end 186. As the acme screw 142 moves the detector head 112 downward, the first chain first end 176 moves downward allowing the first chain second end 186 to move downward only by a like amount.

To prevent the detector head free end from canting or sagging toward the periphery when the inner gantry is rotated 180°, a second leaf chain or other flexible member 190 has a first end 192 fixed to the free end slide carriage. The second chain extends parallel to the guide member 138 and around a sprocket or pulley means 194 that is fixedly mounted to the inner gantry 110. The second chain passes over sprockets or pulley means (not shown) behind sprocket or pulley means 180, 182, 184 and extends parallel to the guide member 134 to a second end 196 which is fixedly connected to the driven slide carriage 132.

When the first detector head is rotated 180° to the position of detector head 114 in FIG. 8, the first chain 174 becomes slack and carries no load. The second chain 190 carries the full load.

In other rotational positions, the load is supported by one or both of the first and second chains. As the guide members 134, 138 approach horizontally, the load on the chains 174, 190 and the acme screw 142 is reduced because more of the weight is supported by the linear guides. In the 90° rotated or horizontal position, all of the weight is supported on the linear guides and no load is supported by the acme screw or either chain.

In alternate embodiments, the preferred leaf chains can be replaced by wire cable, roller chains, or the like. The acme screw radial drive could be replaced with a ball screw, rack and pinion drive, or other drive device. Moreover, both the rotational and translating drive could be manually operated.

Figure 10:
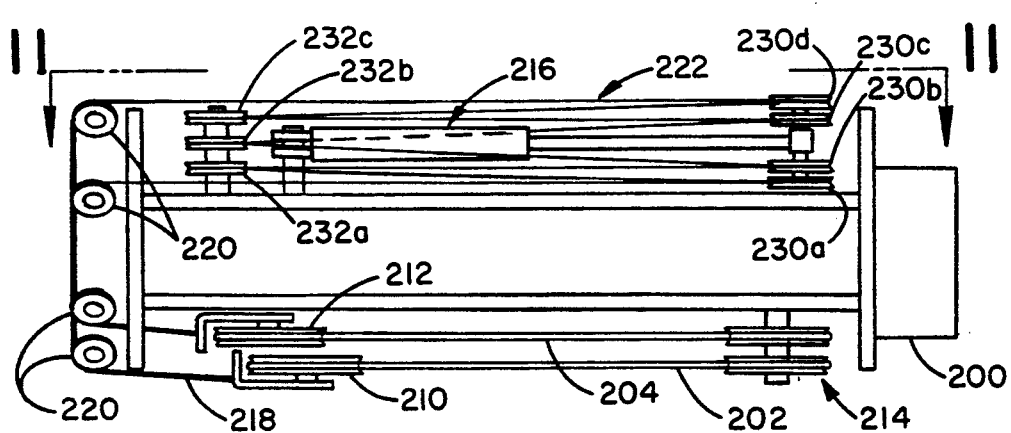
FIG. 10 is a view in partial section with inner gantry removed of the cable take up arrangement of FIG. 9; veiwed from line 10—10 of FIG. 9
Figure 9:
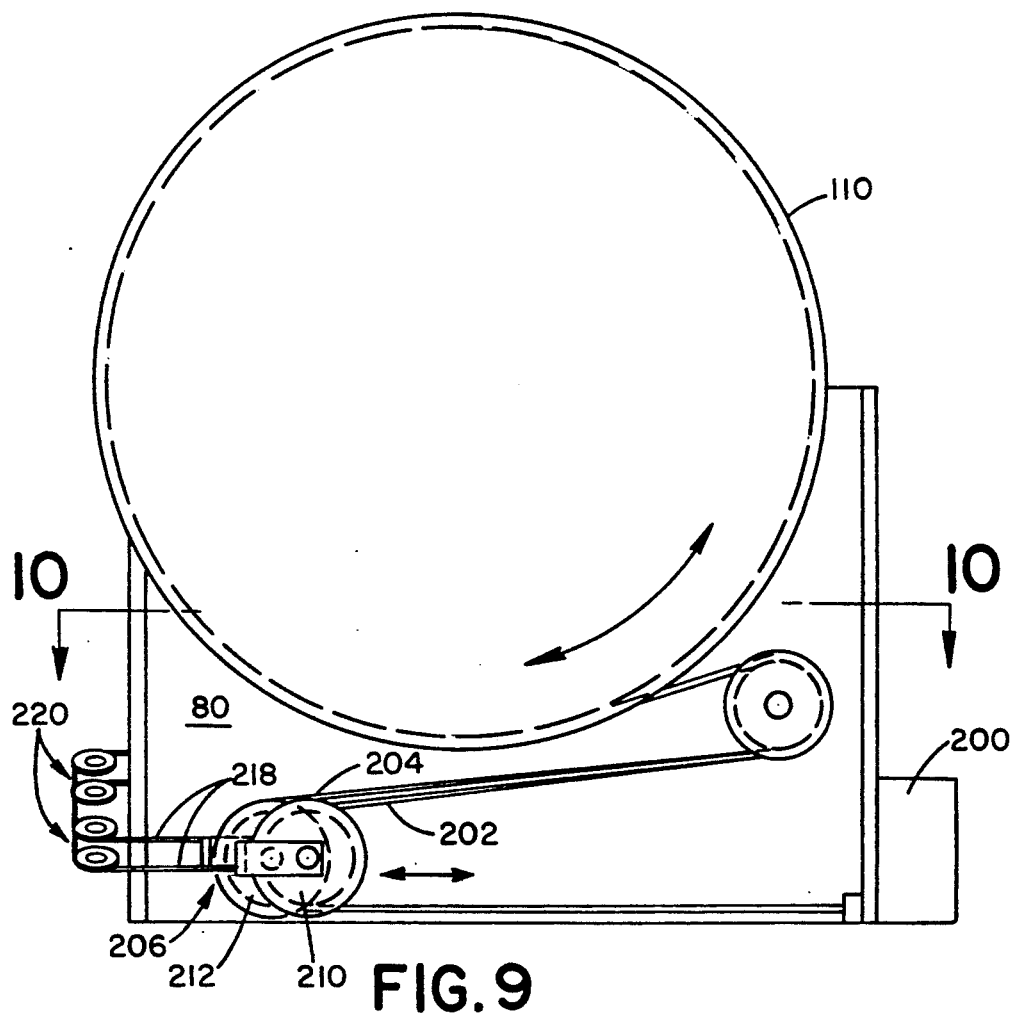
FIG. 9 is a diagrammatic illustration of a cable take up arrangement for maintaining tension on detector head cables in the gantry of FIG. 1.
Figure 11:
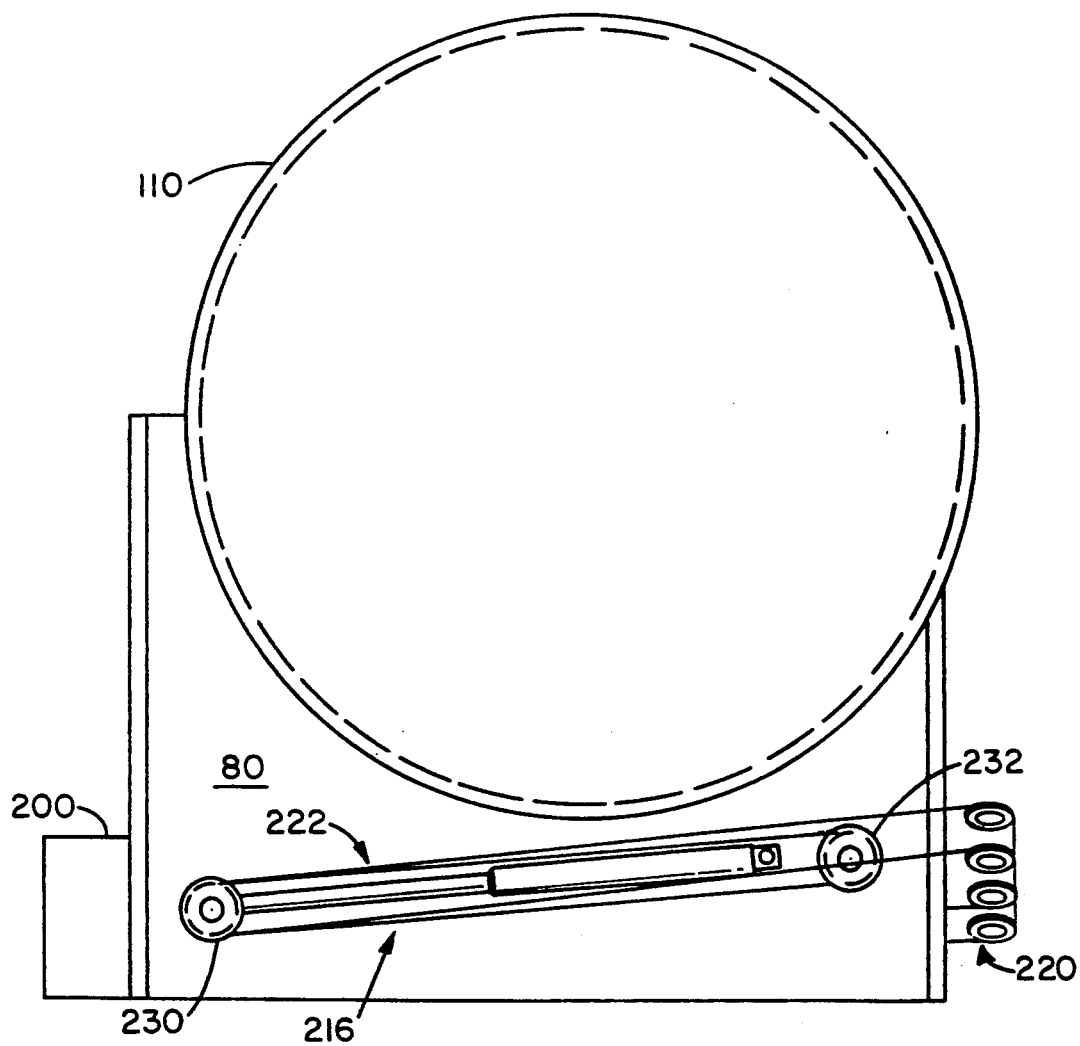
FIG. 11 is illustrative of a gas spring portion of the take up arrangement of FIG. 9 viewed from line 11—11 of FIG. 10.

With reference to FIGS. 9, 10, and 11, associated electronics 200 are connected by cables 202, 204 with detector heads 112 and 114, respectively. As the inner gantry so moves rotationally, the distance between the detector heads and the associated electronics changes. A take up assembly 206 maintains tension on both cables 202 and 204 as the inner gantry is moved rotationally.

More specifically, pulleys or rollers 210, 212 around which cables 202, 204 pass guide the cables along a cable trough 214. A spring means 216, specifically a gas spring, maintains a constant tension or pressure on the pulleys 210, 212 such that the cables are held under constant tension. More specifically, first and second ends of a continuous, flexible means or wire rope 218 are connected with the first and second pulleys 202, 204, respectively. Guide pulleys 220 guide the wire rope to a block and tackle means 222 which produces reduction in spring travel and force. The two ends of the wire rope pulls the two pulleys or rollers 210, 212 independently with about one eighth of the force produced by the gas spring 216. The force reduction is the result of the block and tackle means 222 connected with one end of the gas spring.

More specifically, the block and tackle means includes four pulleys 230a, 230b, 230c, 230d connected with the moving end of the gas spring. Three more pulleys 232a, 232b, 232c are disposed adjacent the closest guide pulleys 220. The wire rope 218 passes back and forth between pulleys 230 and 232 such that eight strands of the wire rope extend between the moveable and fixed ends of the gas spring. With this arrangement with eight strands of wire rope in the block and tackle means, the gas spring piston rod moves ⅛ inch for each inch of cable roller motion. When both cable rollers are moving in the same direction at the same speed, the gas spring will move at a quarter of the speed. The force generated by the gas spring is shared equally by the eight strands of wire rope reducing the spring force to an eighth.

Figure 12:
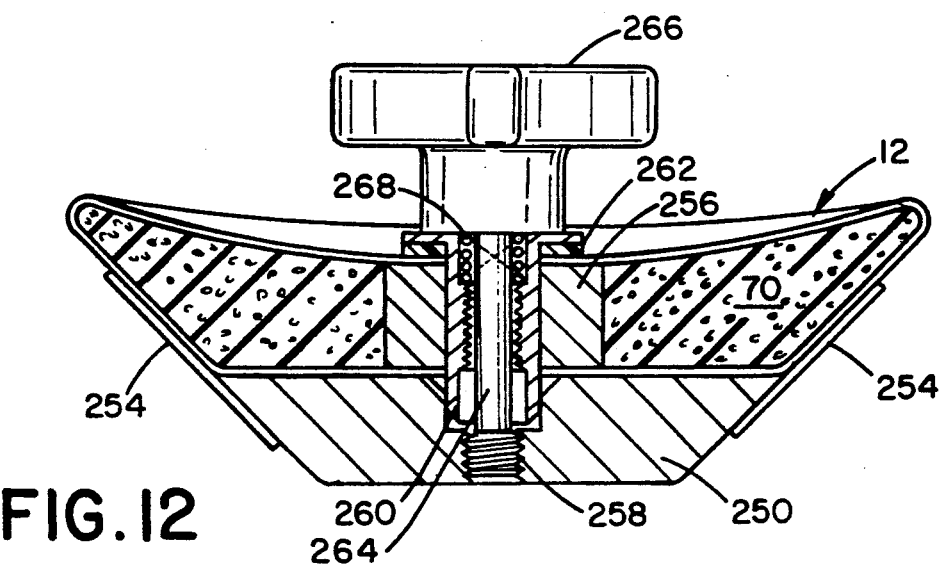
FIG. 12 is an alternate embodiment of the top head end latching arrangement.

With reference to FIG. 12, in an alternate embodiment of the top head end mounting means, a head support arm 250 has one or more side flanges 254 for positioning the head end of the table top more accurately. The head end of the patient table includes a rigid, relatively incompressible block 256 through which a bore extends. The head end support arm 250 has a matching bore with a threaded portion 258. A spring loaded hand knob assembly is received in the table top and support arm bores for clamping the table top 12 and support arm 250 rigidly together. In the illustrated embodiment, the spring loaded hand knob assembly includes a flanged shaft portion 260 which is snugly received in the bores and which presses a nylon washer 262 against an upper surface of the table top. A threaded central shaft 264 and hand knob 266 are spring biased against the flanged shaft portion 262 for selectively pressing the shaft portion 260 against a spring 268 and turning the threaded shaft 264 into the receiving threaded bore portion 258.

The invention has been described with reference to the preferred embodiments. Obviously, modifications and alterations will occur to others upon reading and understanding the preceding specification. It is intended that the invention be construed as including all such alterations and modifications insofar as they come within the scope of the appended claims or the equivalents thereof.

Having thus described the preferred embodiments, the invention is now claimed to be:

1. A nuclear camera system comprising:
   a moveable gantry mounted for horizontal translating movement along a horizontal path;
   a detector head supporting means having a central aperture therethrough for supporting and movably positioning at least one detector head relative to the central aperture; and
   a patient table assembly including a first stationarily mounted pedestal, a second stationarily mounted pedestal, and a patient table top rigidly mounted at opposite ends to the first and second pedestals, the table top passing through the detector head supporting means central aperture, the patient table first pedestal including:
   a generally horizontal first arm member rigidly mounted thereto for receiving a lower surface of the table top on an upper surface thereof;
   an upper flange member disposed adjacent the arm member for engaging an upper surface of the table top, the flange member and arm member being spaced commensurate with a thickness of the table top to define a slot for receiving a first end of the table top snugly therein.

2. The camera system as set forth in claim 1 further including an alignment member connected with one of the (1) table top first end and (2) the flange and first arm members and a slot defined in the other for selectively receiving the alignment member as the table top first end is inserted between the first arm and flange members.

3. The camera system as set forth in claim 1 wherein the arm member has a recess disposed below the slot to facilitate receiving the table first end at an angle to horizontal.

4. The camera system as set forth in claim 1 wherein the second pedestal defines a second arm for receiving a lower surface of a second end of the table top and a clamping means for selectively clamping the table top second end to the second arm.

5. The camera system as set forth in claim 4 wherein the clamping means includes a slide member that extends to engage and hold the top second end fixedly against the second arm and which is selectively retractable to release the top second end.

6. A nuclear camera system wherein comprising:
   a moveable gantry mounted for horizontal translating movement along a horizontal path;
   a detector head supporting means having a central aperture therethrough for supporting and movably positioning at least one detector head relative to the central aperture;
   a patient table top passing through the detector head supporting means central aperture;
   a first pedestal which defines a generally horizontal slot with a width commensurate with a thickness of a first end of the table top, the table top first end being received in the slot;
   a second pedestal which defines an arm for receiving a lower surface of a second end of the table top and a clamping means for selectively clamping the table top second end to the second arm, such that the table top is rigidly mounted to the pedestals.

7. The camera system as set forth in claim 6 wherein the clamping means includes a slide member that extends to engage and hold the top second end fixedly against the second arm and which is selectively retractable to release the top second end.

8. A nuclear camera system comprising:
   a moveable gantry mounted with a mounting system for horizontal translating movement along a generally horizontal path, the mounting system including:
   first and second wheels mounted adjacent a first side of the gantry,
   a carriage member pivotally mounted to the gantry adjacent a second side of the gantry, at least two additional wheels rotatably mounted to the carriage member, and means for limiting pivotal movement of the carriage member relative to the gantry, whereby the first and second wheels and the two additional carriage wheels all remain in gantry supporting contact with the horizontal path even when the horizontal path undulates or is out of level;
- a detector head supporting means having a central aperture therethrough for supporting and movably positioning at least one dectector head relative to the central aperture; and
- a patient table assembly including a first stationarily mounted pedestal, a second stationarily mounted pedestal, and a patient table top mounted at opposite ends to the first and second pedestals, the table top passing through the detector head supporting means central aperture.

9. The camera system as set forth in claim 8 wherein the pivotal movement limiting means includes an extension extending from one of the pivotal member and the gantry and an extending member receiving aperture defined in the other.

10. A nuclear camera system set forth in claim 1 further comprising:
- a moveable gantry mounted for horizontal translating movement along a horizontal path;
- a detector head supporting means having a central aperture therethrough for supporting and movably positioning at least one detector head relative to the central aperture, the detector head supporting means including:
  - a pair of parallel mounted guide members mounted for rotation around the central aperture in a plane transverse to an axis of the central aperture,
  - a driven side slide connected with the detector head and slidably received on one of the guide members,
  - a free side slide connected with an opposite side of the detector head and slidably received on the other guide member,
  - a driving means for selectively driving the driven slide along the guide member,
  - a canting preventing means for preventing the free side of the detector head from canting under gravity relative to the driven side;
- a patient table assembly including a first stationarily mounted pedestal, a second stationarily mounted pedestal, and a patient table top mounted at opposite ends to the first and second pedestals, the table top passing through the detector head supporting means central aperture.

11. The camera system as set forth in claim 10 wherein the canting preventing means includes a first flexible member extending from the driven side parallel to the guide members toward and around a more centrally mounted pulley means, around a peripheral end of the detector head, and parallel to the guide means to the driven side, whereby the first flexible means prevents the detector head free side from canting toward a central portion of the guide members.

12. The camera system as set forth in claim 11 wherein the canting preventing means further includes a second flexible member extending from the free side parallel to the guide means, toward and around a more centrally mounted pulley means, around a peripheral end of the detector head, and parallel to the guide members to the driven side, whereby the second flexible member prevents the free side from canting toward the peripheral end.

13. The camera system as set forth in claim 10 further including:
- first and second electrical cables extending between the detector head supporting means and stationary electronics; and
- a take up means for providing a constant tension to the first and second cables as the detector head moves.

14. A camera system comprising:
- a moveable gantry mounted for horizontal translating movement along a horizontal path;
- a detector head supporting means having a central aperture therethrough for supporting and movably positioning at least one detector head relative to the central aperture;
- first and second electrical cables extending between the detector head supporting means and stationary electronics;
- a take up means for providing a constant tension to the first and second cables as the detector head moves, the take up means including:
  - a first roller over which the first cable passes;
  - a second roller over which the second cable passes;
  - a flexible wire rope means having one end connected with the first roller and a second end connected with the second roller;
  - a spring means for biasing at least a first pulley means over which a generally central portion of the wire rope means passes to provide tension on the first and second rollers;
- a patient table assembly including a patient table top mounted to pass through the detector head supporting means central aperture.

15. The camera system as set forth in claim 14 wherein the spring means includes a gas spring.

16. The camera system as set forth in claim 15 further including a block and tackle means operatively connected with the wire rope and the first pulley means for reducing a ratio between extension of the gas spring and movement of the first and second rollers.

17. The camera system as set forth in claim 14 further including a block and tackle means operatively connected with the wire rope and the first pulley means for reducing the ratio between extension of the spring means and movement of the first and second rollers.

18. The camera system as set forth in claim 14 wherein the detector head supporting means includes:
- a pair of parallel mounted guide members mounted for rotation around the table top in a plane transverse to the table top;
- a driven side slide connected with the detector head and slidably received on one of the guide members;
- a free side slide connected with an opposite side of the detector head and slidably received on the other guide member;
- a driving means for selectively driving the driven slide along the guide member.

19. A nuclear camera system comprising:
- an outer gantry mounted on a plurality of wheels for translating movement along a horizontal path, the plurality of wheels including:
  - at least first and second wheels nonpivotally mounted to the outer gantry for rollingly supporting the outer gantry on the horizontal path,
  - a pivotal member pivotally connected to the outer gantry, at least two additional wheels rotatably mounted to the pivotal member for rollingly supporting the outer gantry on the horizontal path, such that the pivoted member pivots to assure that the two additional wheels continue to engage the horizontal path even when the horizontal path is out of level or undulates, and means for limiting pivotal movement of the pivotal member relative to the outer gantry;

a means having a central aperture therethrough for supporting and movably positioning at least one detector head relative to the central aperture; and a patient table means for selectively supporting a patient in the central aperture.

20. A nuclear camera system comprising:

an outer gantry;

an inner gantry rotatably mounted on the outer gantry, the inner gantry including first and second parallel mounted guide members for movably supporting opposite ends of at least one detector head for movement therealong and means for selectively driving a first side of the detector head along the guide members, the second side of the detector head being mounted to the guide member for free, undriven movement relative thereto, and a canting preventing means for preventing the free side of the detector head from canting relative to the driven side under gravity;

a patient table means for selectively supporting a patient adjacent the detector head.

21. The camera system as set forth in claim 20 wherein the canting preventing means includes a first flexible member extending from the driven side parallel to the guide members toward and around a more centrally mounted pulley means, around a peripheral end of the detector head, and parallel to the guide means to the driven side, whereby the first flexible means prevents the detector head free side from canting toward a central portion of the guide members.

22. The camera system as set forth in claim 21 wherein the canting preventing means further includes a second flexible member extending from the free side parallel to the guide means, toward and around a more centrally mounted pulley means, around a peripheral and if the detector head, and parallel to the guide members to the driven side, whereby the second flexible member prevents the free side from canting toward the peripheral end.

23. The camera system as set forth in claim 20 further including:

a first cable extending from the inner gantry over a first roller to the outer gantry;

a second cable extending from the inner gantry over a second roller to the outer gantry;

a flexible wire rope means having one end connected with the first roller and a second end connected with the second roller;

a spring means for biasing at least a first pulley means over which a generally central portion of the wire rope means passes to provide tension on the first and second rollers while allowing the first and second rollers to move independently.

24. A camera system comprising:

an outer gantry;

an inner gantry mounted for rotation relative to the outer gantry, the inner gantry movably supporting at least one detector head thereon;

a first cable extending from the inner gantry over a first roller to the outer gantry;

a second cable extending from the inner gantry over a second roller to the outer gantry;

a flexible wire rope means having one end connected with the first roller and a second end connected with the second roller;

a spring means for biasing at least a first pulley means over which a generally central portion of the wire rope means passes to provide tension on the first and second rollers while allowing the first and second rollers to move independently;

a patient table means for selectively supporting an examined patient adjacent the detector head.

25. The camera system as set forth in claim 24 wherein the spring means includes a gas spring.

26. The camera system as set forth in claim 25 further including a block and tackle means operatively connected with the wire rope and the first pulley means for reducing a ratio between extension of the gas spring and movement of the first and second rollers.

27. The camera system as set forth in claim 24 further including a block and tackle means operatively connected with the wire rope and the first pulley means for reducing the ratio between extension of the spring means and movement of the first and second rollers 28. The camera system as set forth in claim 24 wherein the patient table means includes:

a table top having a body supporting portion in a first plane and a head supporting portion in an offset, parallel plane;

a foot end support stand to which a foot end of the patient table top is selectively, rigidly fixed;

a head end support stand to which the table top head end is selectively, rigidly fixed.

29. The camera system as set forth in claim 28 wherein the outer gantry is mounted to at least two wheels adjacent a first side and having a pivotal mounted wheel carriage adjacent a second side.

30. A nuclear camera assembly comprising:

a moveable gantry mounted for horizontal translating movement along a horizontal path;

a detector head supporting means having a central aperture therethrough for supporting and movably positioning at least one detector head relative to the central aperture;

a first pedestal which supports a generally horizontal first arm member adjacent an upper end thereof;

an upper flange member disposed adjacent the arm member, the flange member and first arm member being spaced to define a slot therebetween;

a second pedestal having a second generally horizontal arm member mounted adjacent an upper end thereof;

a table top extending through the central aperture, the table top having a first end snugly received in the slot and a second end supported by the second arm member;

a means for releasably securing the table top second end to the second arm member.

31. The assembly as set forth in claim 30 further including an alignment member connected with one of the first arm member and the table top and a slot defined in the other for selectively receiving the alignment member as the table first end is inserted in the slot.

32. The assembly as set forth in claim 30 wherein the second end securing means includes a slide member that extends to engage and hold the top second end fixedly against the second arm and which is selectively retractable to release the top second end.

33. The assembly as set forth in claim 30 wherein the table top has a relatively wide body receiving portion adjacent the first end, a relatively narrow head receiving portion adjacent the second end, the head and body receiving portions being in offset planes and being interconnected by a neck portion.

34. A nuclear camera system comprising:
a means for defining a horizontal path;
a gantry which undergoes horizontal translating movement along the horizontal path;
a detector head supporting means having a central aperture therethrough, the detector head supporting means being mounted for rotation around a central axis of the aperture relative to the gantry, the detector head supporting means supporting at least one detector head such that the detector head is moveable toward and away from the central axis of the aperture and such that the camera head is selectively tiltable to face at least parallel to the central axis and perpendicular to the central axis;
a table top extending through the central aperture;
a first pedestal having a generally horizontally extending first arm member which is releasably and rigidly secured to a first end of the table top;
a second pedestal having a second generally horizontal arm member which is releasably and rigidly secured to a second end of the table top, whereby the rigid securement of the pedestals to the table top locks the table top and the first and second pedestals from folding.

* * * * *